(12) United States Patent
Atkinson et al.

(10) Patent No.: US 11,096,690 B2
(45) Date of Patent: *Aug. 24, 2021

(54) WOUND CLAMP

(71) Applicant: INNOVATIVE TRAUMA CARE, INC., San Antonio, TX (US)

(72) Inventors: Ian Atkinson, Cochrane (CA); Dennis Filips, Ottawa (CA); Prasanna Lakshminarasimhan, Edmonton (CA); Steve Dralle, San Antonio, TX (US); Kelly Moffet, Edmonton (CA)

(73) Assignee: Innovative Trauma Care, Inc., San Antonio, TX (US)

( * ) Notice: Subject to any disclaimer, the term of this patent is extended or adjusted under 35 U.S.C. 154(b) by 147 days.

This patent is subject to a terminal disclaimer.

(21) Appl. No.: 16/287,875

(22) Filed: Feb. 27, 2019

(65) Prior Publication Data
US 2019/0290276 A1    Sep. 26, 2019

Related U.S. Application Data

(63) Continuation of application No. 14/103,641, filed on Dec. 11, 2013, now abandoned, and a
(Continued)

(51) Int. Cl.
*A61B 17/08*    (2006.01)
*A61M 25/02*    (2006.01)
*A61B 90/57*    (2016.01)

(52) U.S. Cl.
CPC ............ *A61B 17/08* (2013.01); *A61B 17/083* (2013.01); *A61B 90/57* (2016.02); *A61M 25/02* (2013.01);
(Continued)

(58) Field of Classification Search
CPC ........ A61B 2017/081; A61B 2017/088; A61B 17/08; A61B 17/083; A61B 17/085;
(Continued)

(56) References Cited

U.S. PATENT DOCUMENTS 2,881,762 A    4/1959 Lowrie
3,068,869 A    12/1962 Hunter et al.
(Continued)

FOREIGN PATENT DOCUMENTS

GB    456458    11/1936
SU    1287858    2/1987
(Continued)

OTHER PUBLICATIONS

International Search Report regarding PCT/IB2013/003178.
(Continued)

*Primary Examiner* — Majid Jamialahmadi
(74) *Attorney, Agent, or Firm* — DLA Piper LLP (US)

(57) ABSTRACT

The present disclosure provides a wound closure device including: (a) a first opposing member and a second opposing member disposed on opposing sides of a central axis, each resiliently moveable between a closed position and open position relative to each other, each of the opposing members having a distal edge; (b) skin penetrating means for anchoring the device; (c) a pressure bar along each distal edge; (d) releasable locking means for biasing or maintaining the device in the closed position; and optionally (e) an accessory component.

15 Claims, 26 Drawing Sheets

Related U.S. Application Data continuation-in-part of application No. 13/877,897, filed as application No. PCT/CA2011/001170 on Oct. 19, 2011, now Pat. No. 9,307,990.

(60) Provisional application No. 61/735,893, filed on Dec. 11, 2012, provisional application No. 61/394,566, filed on Oct. 19, 2010.

(52) U.S. Cl.
CPC ... *A61B 2017/081* (2013.01); *A61B 2217/005* (2013.01); *A61M 2025/024* (2013.01); *A61M 2025/028* (2013.01); *A61M 2025/0286* (2013.01)

(58) Field of Classification Search
CPC ............ A61B 90/57; A61M 2025/024; A61M 2025/028; A61M 2025/0286; A61M 25/02
See application file for complete search history.

(56) References Cited

U.S. PATENT DOCUMENTS

| | | | |
|---|---|---|---|
| 4,317,451 | A | 3/1982 | Cerwln et al. |
| 4,505,274 | A | 3/1985 | Speelman |
| 4,535,772 | A | 8/1985 | Sheehan |
| 4,832,027 | A | 5/1989 | Utz |
| 5,486,196 | A | 1/1996 | Hirshowitz et al. |
| 6,013,027 | A | 1/2000 | Kahn et al. |
| 6,113,536 | A * | 9/2000 | Aboul-Hosn ...... A61B 17/0206 600/227 |
| 8,323,313 | B1 | 12/2012 | Belson et al. |
| 2002/0173807 | A1 | 11/2002 | Jacobs |
| 2004/0267309 | A1 | 12/2004 | Garvin |
| 2005/0251204 | A1 * | 11/2005 | Attinger ............... A61B 17/083 606/221 |
| 2008/0139879 | A1 | 6/2008 | Olson et al. |
| 2009/0182374 | A1 | 7/2009 | Keith |
| 2011/0028797 | A1 | 2/2011 | Yee et al. |
| 2011/0106148 | A1 | 5/2011 | Ginn et al. |
| 2012/0046582 | A1 | 2/2012 | Hopman et al. |

FOREIGN PATENT DOCUMENTS

| | | |
|---|---|---|
| SU | 130138 | 4/1987 |
| SU | 1377054 | 2/1988 |
| SU | 1405825 | 6/1988 |
| WO | WO 199426173 | 11/1994 |
| WO | WO 199528886 | 11/1995 |
| WO | WO 2009096860 | 8/2009 |
| WO | WO 2012051706 | 4/2012 |

OTHER PUBLICATIONS

Australian Examination Report dated Apr. 18, 2018 regarding AU 2017201066.
Dictionary.com definition for "resiliency".
IN Office Action in Indian Application No. 3404/CHENP/2013, dated Jul. 11, 2019, 6 pages.
IN Office Action in Indian Application No. 3541/CHENP/2015, dated Mar. 11, 2021, 7 pages.
Partial Supplementary European Search Report dated Jul. 29, 2016 regarding EP 13 86 1908.
Russian Office Action (with English translation) dated May 7, 2015 regarding patent application No. RU 2013122861/14.
Russian Office Action (with English translation) dated Nov. 27, 2015 regarding patent application No. RU 2013122861/14.
Russian Office Action dated Jan. 1p, 2017, regarding RU 2013122861/14(033765).

\* cited by examiner

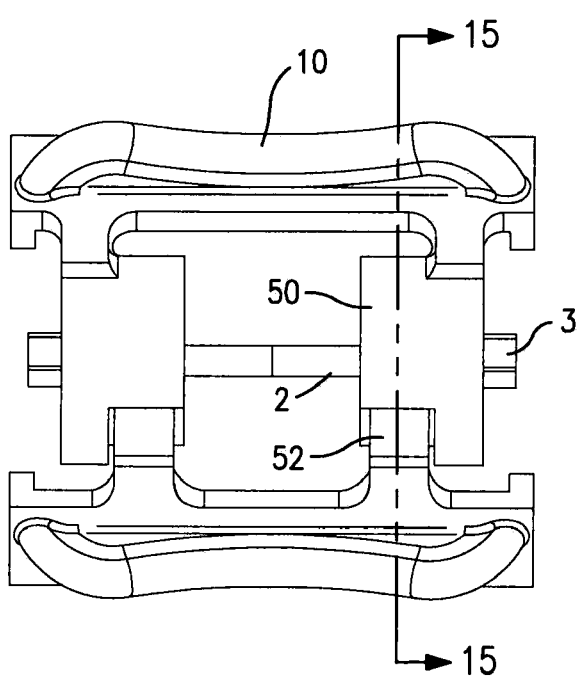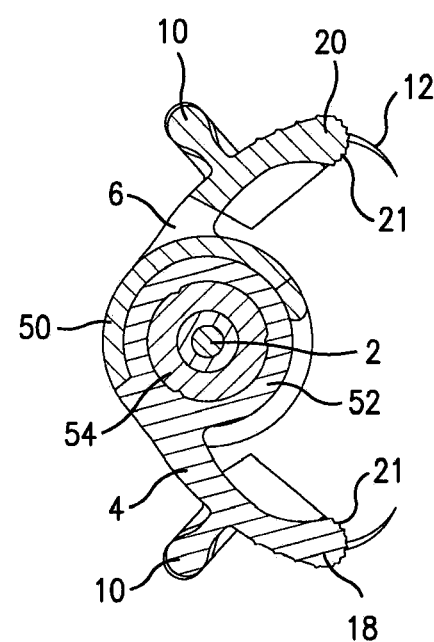
FIG. 14  FIG. 15

WOUND CLAMP

CROSS REFERENCE TO RELATED APPLICATION(S)

This application is a continuation of U.S. application Ser. No. 14/103,641 filed Dec. 11, 2013, now pending and claims the benefit under 35 USC § 119(e) to U.S. Application Ser. No. 61/735,893 filed Dec. 11, 2012; and is a continuation-in-part of U.S. application Ser. No. 13/877,897 filed Apr. 24, 2013, now U.S. Pat. No. 9,307,990, Issued Apr. 21, 2016; which is a 35 USC § 371 National Stage application of International Application No. PCT/CA2011/001170 filed Oct. 19, 2011, now expired; which claims the benefit under 35 USC § 119(e) to U.S. Application Ser. No. 61/394,566 filed Oct. 19, 2010. The disclosure of each of the prior applications is considered part of and is incorporated by reference in the disclosure of this application.

FIELD OF THE INVENTION

The present invention relates to a clamp device for wound closure. In particular, the invention relates to a haemorrhage control device and accessories thereto for closing a wound, particularly in emergency situations, such as during military operations or civilian disaster situations.

BACKGROUND

In both military and non-military emergency medical situations, it is often necessary to temporarily close a wound to prevent bleeding and to avoid contaminating the wound. In many situations, it is impractical to suture or staple a wound closed, which will often take five to ten minutes.

While utilization of strap style tourniquets have been widely accepted for field care, these devices present a number of disadvantages. Tourniquets are slow and difficult to maneuver and place around the extremity. They are limited by how high they can be placed on a limb and do not address major bleeding in the groin or axilla where larger blood vessels run or other areas of the body, such as the trunk, neck, or scalp. They create a lot of pain for the casualty and there is a risk of limb loss when left on too long. Pneumatic tourniquets are less painful but share all of the anatomical restrictions and are less sturdy for military field use.

As an alternative to manual pressure and packing with gauze, hemostatic agents and dressings have been developed to accelerate the clotting process in wounds. One such product, referred to as QuickClot™ (Z-Medica) comprises granular zeolites which are applied to the injured vessel, causing water absorption from the blood to the zeolite to concentrate clotting factors and speed up clot formation. However, the granular form is awkward to apply in a windy environment, and the powder or bandage device is still subject to movement during extraction of the wounded patient, which can loosen the clot and cause leakage through the puncture to increase blood loss. Furthermore, the granular material is very exothermic, to the extent it can cause burns, and is difficult to combine with manual pressure because of the temperature generated. QuickClot™ has since been replaced with Combat Gauze™ (Z-Medica) which is a gauze impregnated with a kaolin substance which is not exothermic and does not have the disadvantages of a granular powder. It takes at least three to five minutes of manual pressure over the hemostatic agent before it is effective.

Even in a field hospital, bleeding from wounds can be problematic when faced with multiple penetration wounds. Penetrating wounds may not appear to bleed because the patient is in shock, but will often commence or resume bleeding upon resuscitation and return of systolic blood pressure. The surgeon often does not have enough time to close multiple wounds before bringing the patient to an operating room for urgent surgery.

Additionally, pre-hospital drainage procedures are becoming more common and varied. It is a well-known technique to apply and fix a tube, such as a drainage tube, through the skin in order to drain fluid or air from a cavity such as the chest. Chest tube insertion (also known as a chest drain, tube thoracostomy or intercostal drain) is the definitive procedure for treating tension pneumothorax and hemothorax, and can be a life-saving procedure.

A common problem is securing the tube to the patient. It is very easy to remove these tubes when in place if not anchored properly. In the pre-hospital setting, inexperienced doctors and paramedics commonly perform insertion and fixation of the tube. These individuals are trained in advanced life support, but rarely have any surgical training to anchor a chest tube properly. Moreover, since trauma mortality is time-sensitive, emergency pre-hospital care requires rapid solutions that sometimes may lead to ineffective fixations. Agitated, hypoxemic patients or those experiencing brain trauma might try to pull the tube out with the risk that poorly anchored tubes can fail.

Current fixation protocols require the tube to be secured to the skin using sutures tied tightly around the tube. However, sometimes these tubes slip through the knot and are pulled out, inadvertently migrating away from the cavity especially during loading and transport of the patient.

It is conventional to anchor tubing to the body of a patient by taping the tubing to the skin or an adhesive based anchoring devices. Tape can easily tear off the skin, thereby releasing the tubing. When blood or fluids are present, many adhesives do not effectively adhere to the skin and risk failure. Surgical incision of the skin of the chest wall with a scalpel to insert the tube likely makes the skin wet with blood, reducing adherence.

Surgical incision in the field by minimally trained individuals reduces the tight fit of the tube to the incision, thus reducing the stability of the tube and potentially allowing it to move, change its angle of penetration, or become disengaged from the chest wall. Reinsertion of an unsanitized tube back into the incision after migration out of the wound may lead to increased infection risk.

Many wound closure devices are known in the art, however, may be improved upon in many different facets. There is a need in the art for a wound closure device which may be convenient to use, is relatively compact, and is effective in closing a wound under difficult situations which may arise in emergency situations, such as during warfare, terrorist attacks, accidents or during natural disasters. A device is also required that can anchor a tube in place at or near the site of a drain that is easy to perform and makes it safer and more secure if the use of the tube is considered in a pre-hospital setting which may be used with a wound closure device.

SUMMARY OF THE INVENTION

The present invention relates to a wound closure device. The device rapidly re-approximates the skin edges by engaging the skin to seal the wound. The device is configured to open and close in a clam-shell configuration, and may be configured to be operated one-handed. In one embodiment, the device comprises needles which puncture the skin edges when the device is closed, and a pressure bar which applies pressure substantially perpendicular to the long axis of the wound. In one embodiment, the pressure bar comprises end closure members which are disposed substantially perpendicular to the pressure bar. The pressure is initially exerted manually by closing the device onto the skin surrounding the wound. The device may be maintained in a closed position by a biasing means, by a ratcheting mechanism, by friction or some other mechanical configuration.

Without restriction to a theory, the applicants believe that by closing the wound tightly between two opposing members, blood loss from the wound can be minimized even if there are significant wounds below the surface of the skin, if the wound is in a compressible zone. The patient may then be transported to a surgical facility with a minimized risk of bleeding out in the meantime. In one embodiment, the end closure members hem in the wound from the ends, further enhancing the closure of the wound.

Control of bleeding is achieved when pressure in or on the wound exceeds arterial or venous pressures. Packing of the wound with gauze or hemostatic agents prior to skin closure may be preferable for some wounds. Since the device seals off the skin from the outside it can also be used to prevent bowel evisceration out of a wound or to treat a sucking chest wound.

Therefore, in one aspect, the invention may comprise a wound closure device comprising: (a) a first opposing member and a second opposing member engaged about a longitudinal axis, each pivotally moveable around the axis between a closed position and an open position relative to each other, and moveable longitudinally along the axis from a first position to a second position, each of the opposing members having a proximal edge adjacent the longitudinal axis and a distal edge, and an outer face and an inner face; (b) a first ratchet on the first member, and a second ratchet on the second member, which engage each other to maintain the opposing members in the closed position, when the first and second members are in the first position, and which disengage when the first and second members are in the second position; and (c) a plurality of needles disposed on the distal edges of the first and second members. In one embodiment, each opposing member comprises an end closure member at each end, which is substantially perpendicular to the distal edge, and is aligned with an end closure member on the other opposing member.

In another aspect, the invention comprises a wound closure device comprising: (a) a first opposing member and a second opposing member engaged about a longitudinal axis, each pivotally moveable around the axis between a closed position and an open position relative to each other, each of the opposing members having a proximal edge adjacent the longitudinal axis and a distal edge; (b) skin penetrating means for anchoring the device; (c) a pressure bar along each distal edge; and (d) releasable means for biasing or maintaining the device in the closed position.

In another aspect, the invention may comprise a wound closure device comprising: (a) a first opposing member and a second opposing member engaged about a longitudinal axis, each pivotally moveable around the axis between a closed position and an open position relative to each other, and moveable longitudinally along the axis from a first position to a second position, each of the opposing members having a proximal edge adjacent the longitudinal axis and a distal edge, and an outer face and an inner face; (b) a first ratchet on the first member, and a second ratchet on the second member, which engage each other to maintain the opposing members in the closed position, when the first and second members are in the first position, and which disengage when the first and second members are in the second position; (c) a plurality of needles disposed on the distal edges of the first and second members; and (d) an accessory component. In one embodiment, each opposing member comprises an end closure member at each end, which is substantially perpendicular to the distal edge, and is aligned with an end closure member on the other opposing member.

In another aspect, the invention comprises a wound closure device comprising: (a) a first opposing member and a second opposing member engaged about a longitudinal axis, each pivotally moveable around the axis between a closed position and an open position relative to each other, each of the opposing members having a proximal edge adjacent the longitudinal axis and a distal edge; (b) skin penetrating means for anchoring the device; (c) a pressure bar along each distal edge; (d) releasable means for biasing or maintaining the device in the closed position; and (e) an accessory component.

In another aspect, the invention comprises a wound closure device comprising: (a) a first opposing member and a second opposing member disposed on opposing sides of a central axis, each resiliently moveable between a closed position and open position relative to each other, each of the opposing members having a distal edge; (b) skin penetrating means for anchoring the device; (c) a pressure bar along each distal edge; (d) releasable locking means for biasing or maintaining the device in the closed position; and optionally (e) an accessory component.

In yet another aspect, the invention provides a method for performing a medical procedure on a subject. The method includes: (a) deploying a wound closure device of the invention to a wound of the subject; and (b) locking the wound closure device in the closed position, thereby performing a medical procedure on the subject. The method may further include coupling a medical instrument to the wound closure device.

BRIEF DESCRIPTION OF THE FIGURES

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIG. 14 is a top view of the embodiment of FIG. 10 in an open position.

FIG. 15 is a cross-sectional view along line 15-15 in FIG. 14.

DETAILED DESCRIPTION

Figure 1:
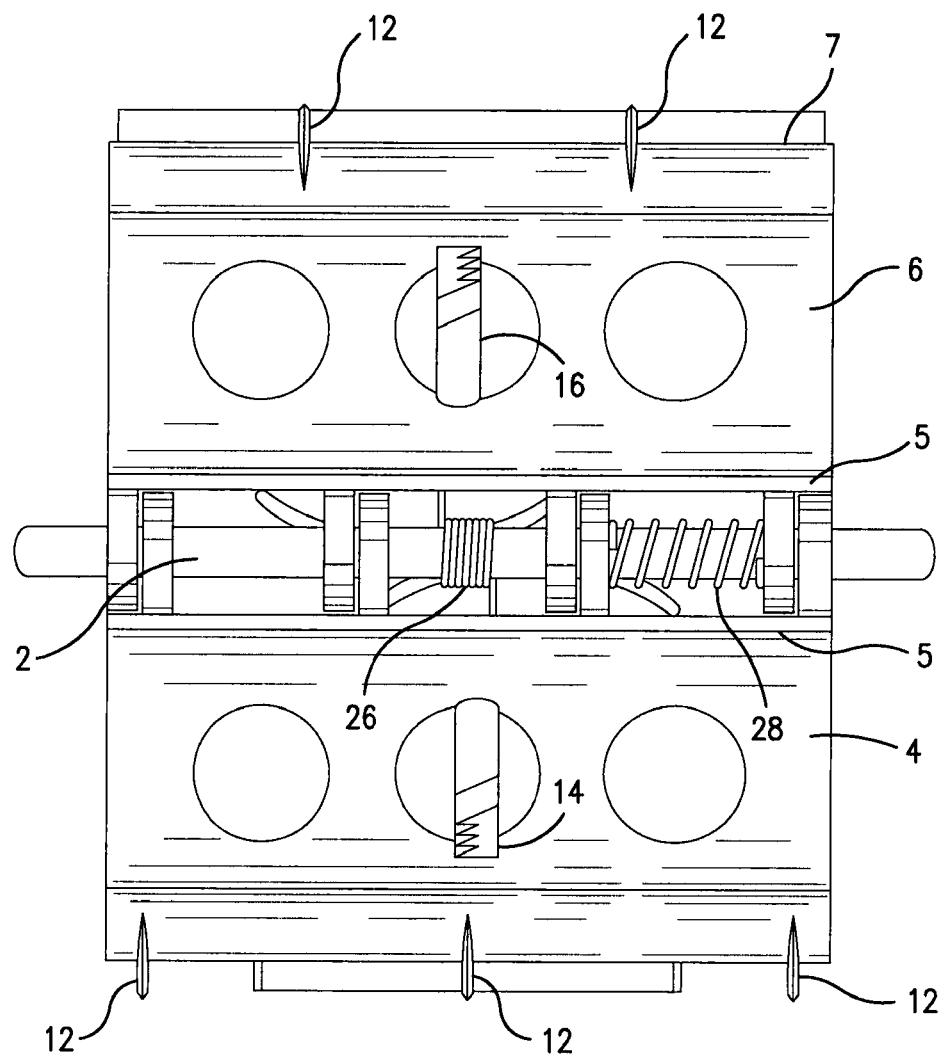
FIG. 1 is a bottom view of one embodiment of a clamp in the full open position.
Figure 2:
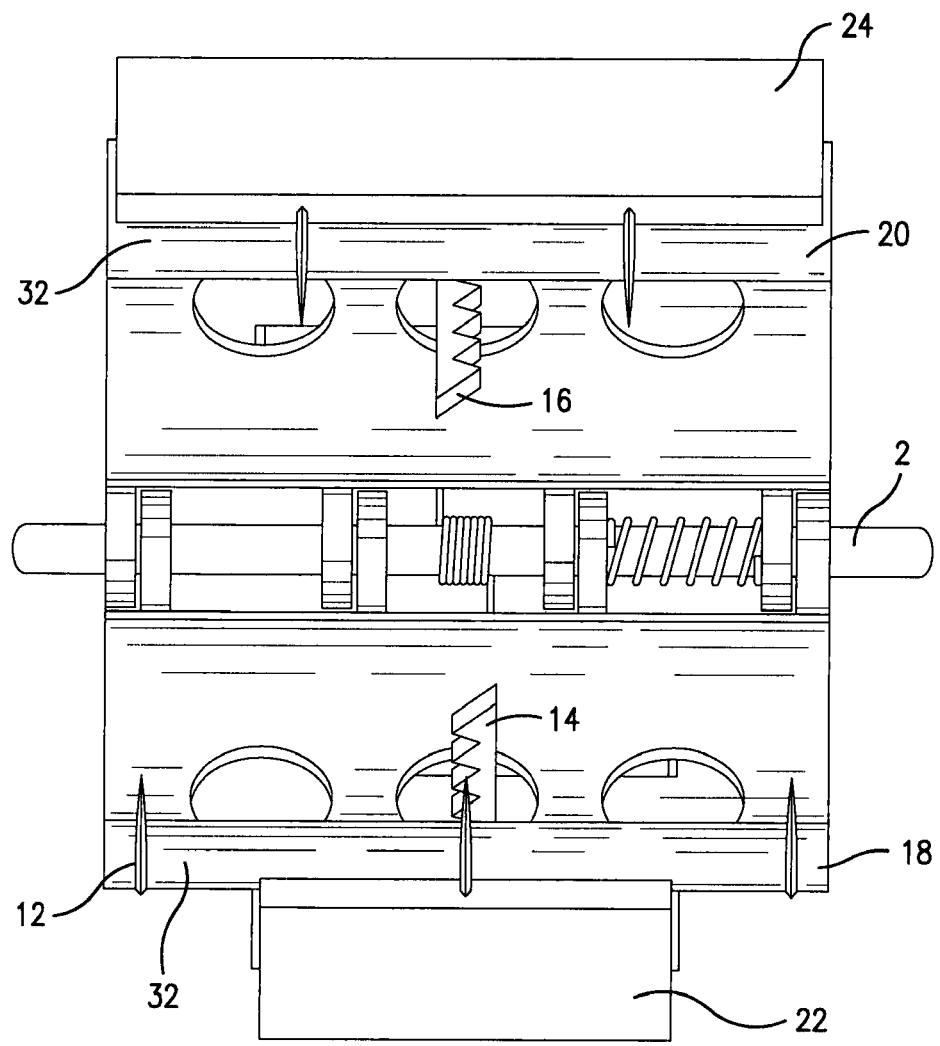
FIG. 2 is a bottom view of a clamp in a partially closed position.
Figure 3:
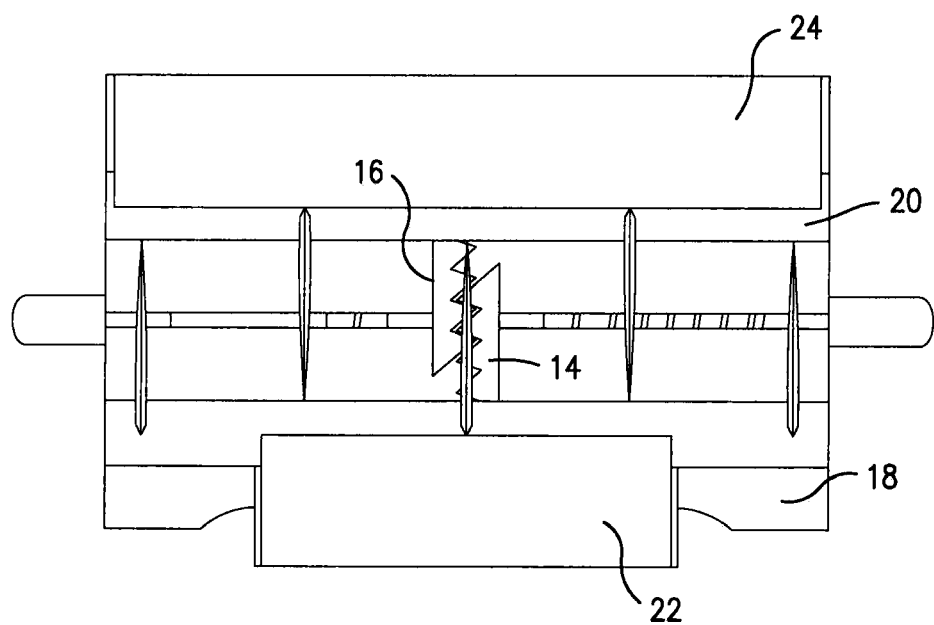
FIG. 3 is a bottom view of a clamp in a fully closed position.

The invention relates to a wound closure device. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

In general terms, one embodiment of the wound closure device is configured in a clamshell type configuration, with a first opposing member (4) and a second opposing member (6) pivotally attached to each other about a pin (2) which defines a longitudinal axis of rotation. Each of the opposing members having an outer face and inner face and two ends. In one embodiment, each opposing member approximates a bisected cylinder which has a proximal edge (5) and a distal edge (7). The longitudinal pivoting axis (2) is adjacent the proximal edge. The two bisected cylinder halves approximate a cylinder when in the closed position, where the two distal edges are proximal to each other. When the first and second members are pivoted to an open position, the two distal edges are spread apart.

While the first and second opposing members (4, 6) are illustrated herein to be half-cylinder sections in the embodiment illustrated, they may be approximated by interconnected curved arms or another equivalent configuration.

In one embodiment, each opposing member comprises an end closure member (8) at each end. Each end closure member (8) is substantially perpendicular to the distal edge, and is aligned with an end closure member on the other opposing member. Preferably, when the device is in a closed position, two opposing end closure members (8) abut each other, or come towards each other, in order to enclose or partially enclose the volume between the two opposing members at each end. In an alternative embodiment, the distal edges (7) may be curved so that the distance between the two distal edges (7) is reduced towards the ends when the device is in a closed position. Either configuration is intended to minimize leakage from the wound from the ends of the wound.

Without restriction to a theory, the applicants believe that by closing the wound tightly, between the two opposing members and between the end closure members, blood loss from the wound can be minimized even if there are significant wounds below the surface of the skin, in a compressible zone of the body. The patient may then be transported to a surgical facility with a minimized risk of bleeding out in the meantime.

Figure 8:
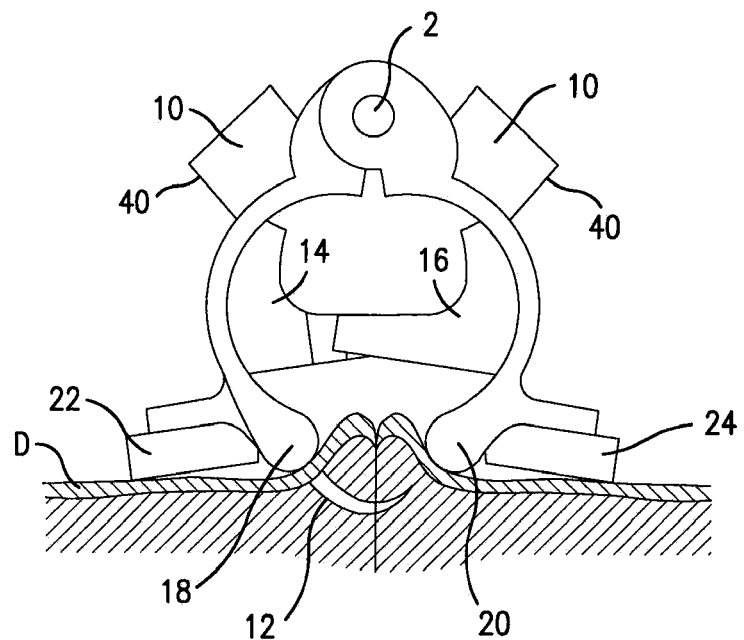
FIG. 8 is an end view of a clamp closed on a wound.

In one embodiment, the opposing members (4, 6) have needles (12) for piercing the skin on opposite sides of the wound. The needles have two primary functions. The first is to anchor the device into place when it is closed in place to seal a wound. If the device were to solely rely on frictional engagement with the skin, it might easily be knocked off. The second is to cause the skin and underlying tissue to bunch up between the opposing members, as is illustrated in FIG. 8. In one embodiment, the needles are long enough to penetrate the dermal layer (D) and extend into the underlying tissue. This action enhances the sealing action of the device.

In one embodiment, the needles (12) are alternately placed along the length of the opposing members such that the needles are interleaved. In one embodiment, the needles are curved such that the piercing of skin and closing of the device brings opposing edges of the wound up into the device, as is illustrated in FIG. 8. As a result, dermis to dermis contact along the length of the wound is promoted, which enhances the seal created by the device. As one skilled in the art will appreciate, the needles may have a radius of curvature similar to that of the first and second members.

In one embodiment, each of the opposing members (4, 6) has a pressure bar (18, 20) along the distal edge (7) of the member. Once the device is closed on a wound, the pressure bars (18, 20) exert relatively even pressure along the length of the wound to close the wound. The pressure bar may comprise frictional elements to help grip the skin, such as ridges (21) which run parallel to the distal edge.

In one embodiment, the pressure bar (18, 20) is configured to interact with or hide the needles of the opposing member in order to prevent exposing the needles when the device is being handled in the closed position. In one embodiment, the pressure bars may be lined with a resilient material (32) which envelops the needle tips, such as neoprene or another rubbery material. The resilient material may also aid in the application of pressure to the wound.

Figure 9:
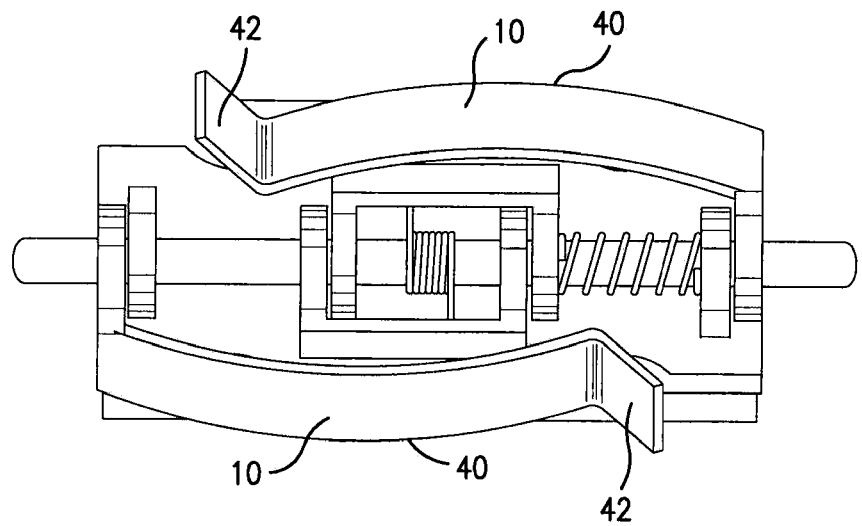
FIG. 9 is a top view of an alternative embodiment of the clamp.

In one embodiment, each of the opposing members (4, 6) has a grip (10) on the outer face. In one embodiment, the grips are raised concave surfaces placed near the pivot axis. The grips each provide a first gripping surface (40) which is substantially parallel to the longitudinal axis, which facilitates a one-handed opening motion. In one embodiment, the grips provide a second gripping surface (42) to push the first and second members apart along the longitudinal axis. The second gripping surface (42) may be substantially perpendicular to the longitudinal axis. Different grip configurations may provide suitable first and second gripping surfaces. In one embodiment, the grips may be optimized for such use, as is shown in FIG. 9.

The device can be stored in a closed position, and is then opened by a user for use. In preferred embodiments, various mechanisms may be used to bias the device into an open position, but allow for storage in a closed position, and also allow for locking into a closed position when the device is in storage or in use. The device may also be stored in an open position. In one embodiments, various mechanisms allow for storage in an open position.

Figure 7A:
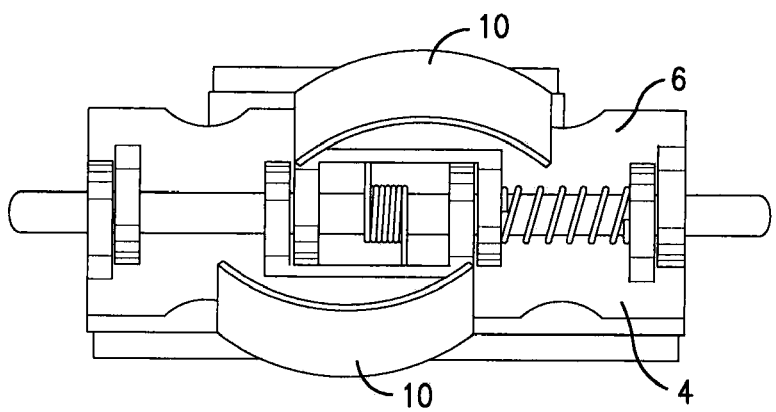
FIG. 7A is a top view of the clamp in the closed position with the ratchets engaged.
Figure 7B:
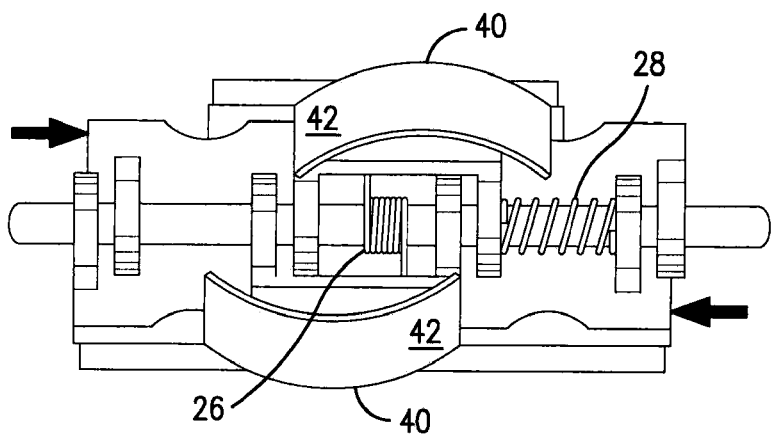
FIG. 7B is a top view of the clamp in the closed position but with the ratchets disengaged, allowing the device to be opened.

In one embodiment, the device may be biased towards its open position by a first spring (26) but is held in the closed position by cooperating ratchets (14, 16) disposed on the inner face of the first and second members. The ratchets (14, 16) are disengaged by moving the first member longitudinally away from the second member, as shown by the arrows in FIG. 7B, allowing the device to be opened. A second spring (28) places longitudinal pressure on the first and second members to keep the ratchets engaged.

Figure 4A:
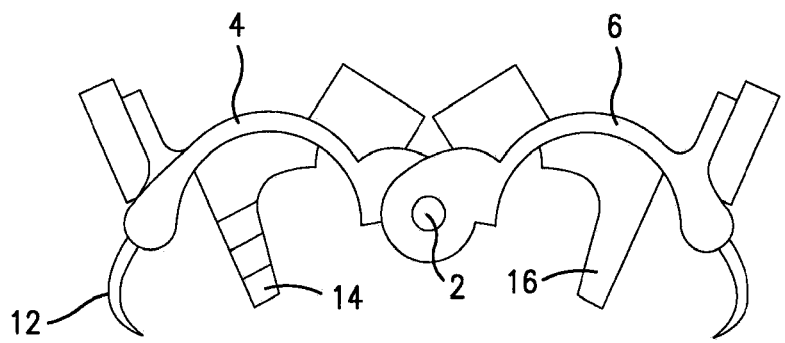
FIGS. 4A, 4B, 4C, 4D are end views of a clamp in an open and partially closed and closed position, respectively.
Figure 4B:
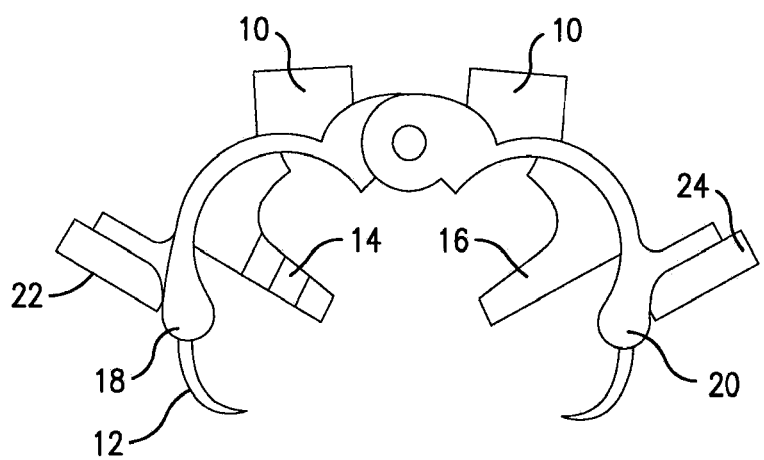
Figure 4C:
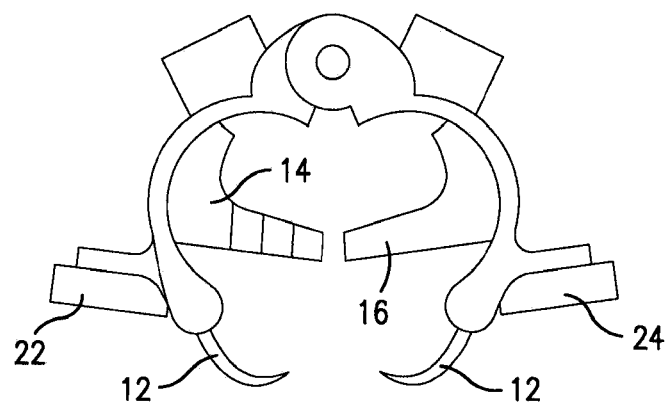
Figure 4D:
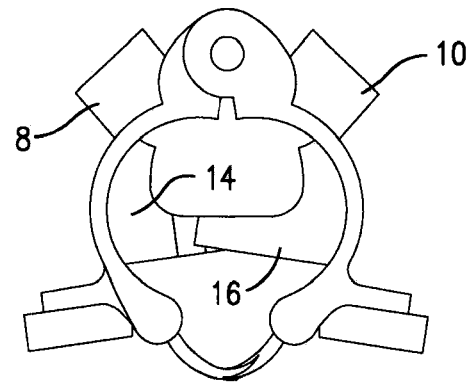
Figure 5:
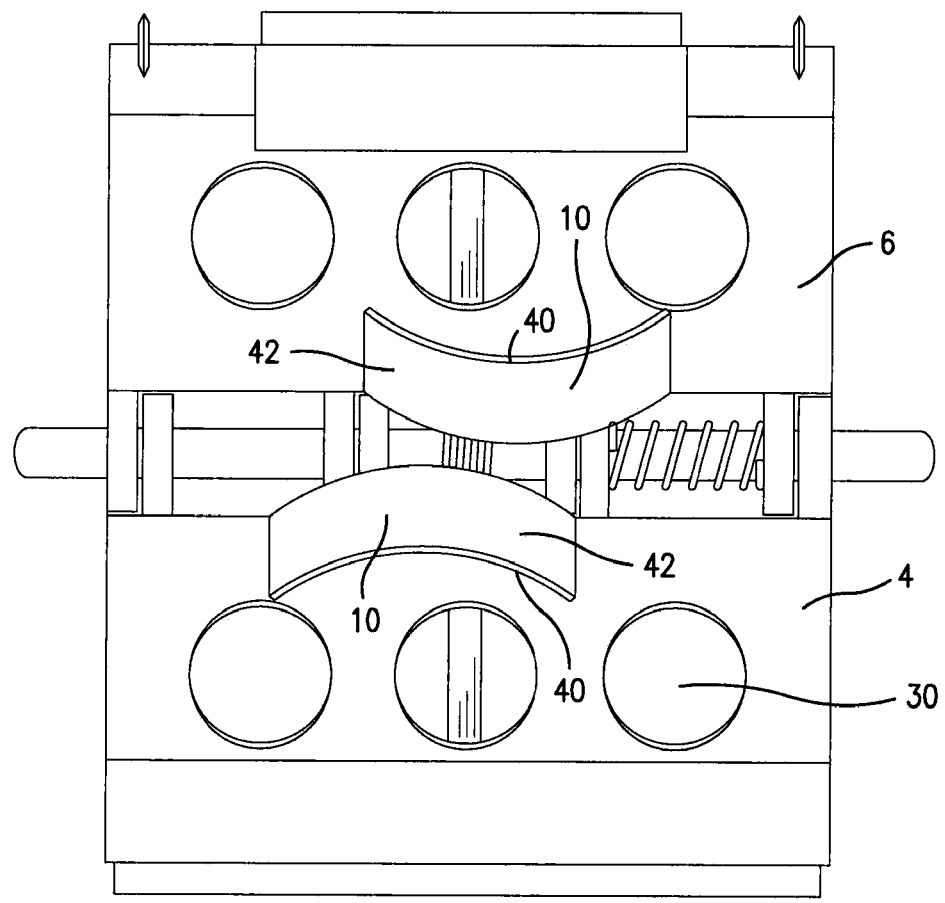
FIG. 5 is a top view of a clamp in a partially closed position.
Figure 6:
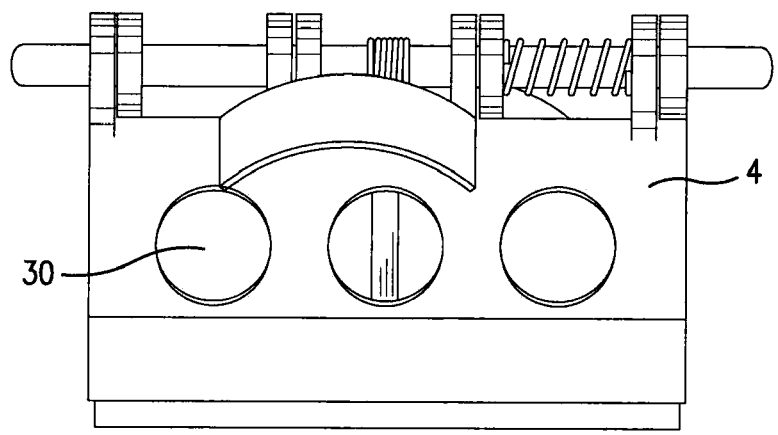
FIG. 6 is a side view of a clamp in a closed position.

A plurality of ratchet teeth on each opposing ratchet permits the user to control the closed position. In the fully closed position, the distal edges of the opposing members are adjacent each other, the opposing needles overlap, and all the ratchet teeth are engaged, as shown in FIG. 4D. The device may be partially closed, such as when placed on a wound, by engaging only the end teeth of the opposing ratchets. Once the device is opened, it may be closed on the wound by forcing the two opposing members closed, against the pressure of the first spring (26), until the opposing ratchets engage each other.

In an alternative embodiment, the surfaces of the two opposing members which rotationally engage each other, about the longitudinal axis, may bear elements which frictionally engage each other. For example, one opposing member may comprise an outer cylindrical surface, while the other comprises an inner cylindrical surface. The two cylindrical surfaces bear against each other, and may provide sufficient friction to maintain the device in a closed position. Frictional elements such as raised ridges on the cylindrical bearing surfaces may provide additional friction.

Figure 10:
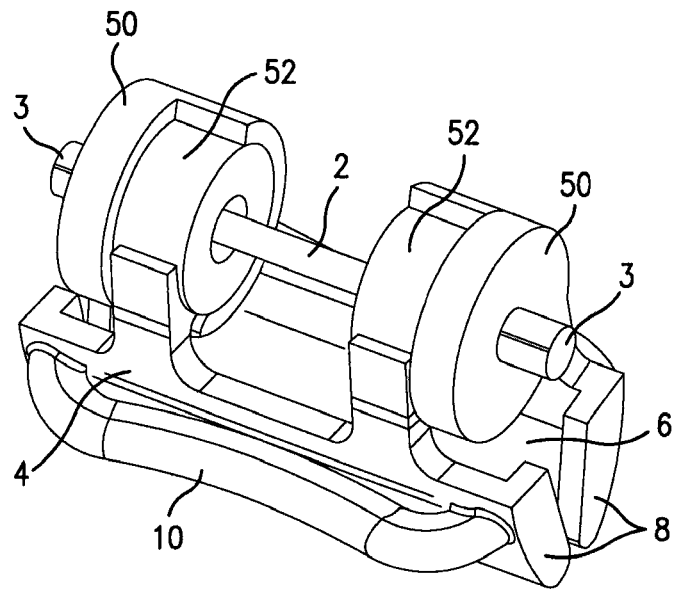
FIG. 10 is a view of a further alternative embodiment of the clamp.
Figure 11:
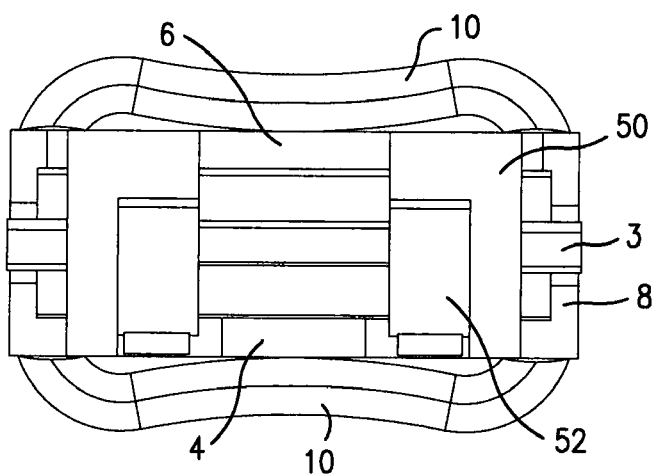
FIG. 11 is a top view of the embodiment of FIG. 10.
Figure 12:
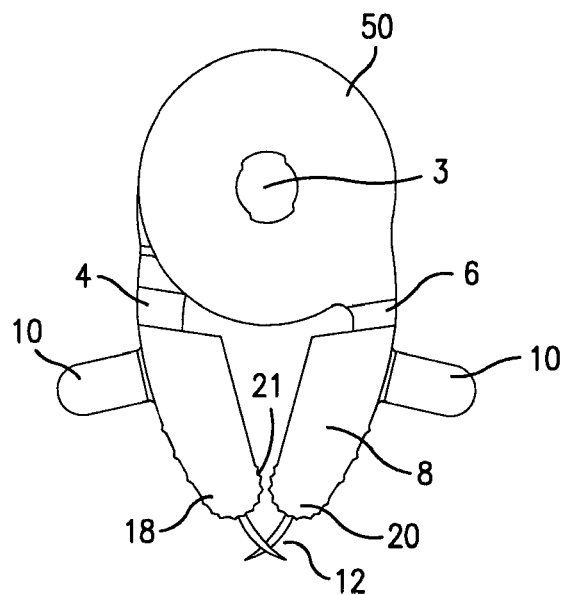
FIG. 12 is an end view of the embodiment of FIG. 10.
Figure 13:
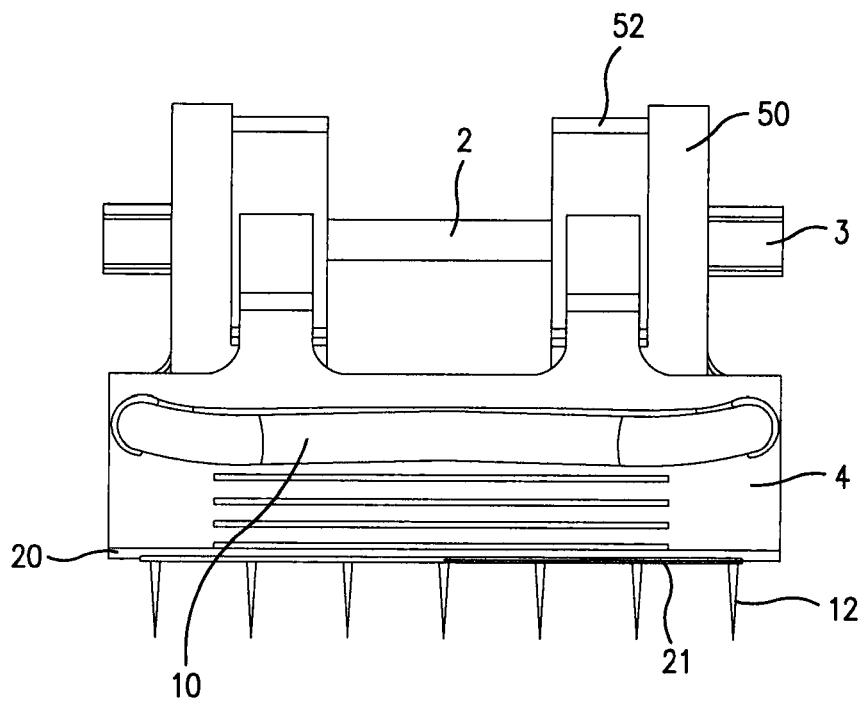
FIG. 13 is a side view of the embodiment of FIG. 10.

In another embodiment, the device comprises a releasable engagement mechanism comprising a one-way bearing. As shown in FIG. 10, the two opposing members (4, 6) rotationally engage each other about an axial pin (2) with a cylindrical bearing. The pin (2) is keyed at each end (3) so as to rotate with an outer cylinder (50) while being moveable in the axial direction. An inner cylinder (52) rotates within the outer cylinder (50). A one-way bearing (54) fits within and is affixed to the inner cylinder and is frictionally engages an engagement section of the pin (2) which passes through the bearing (54). The pin (2) comprises two telescoping sections which are biased outwards with an internal spring, and which can be overcome by pressing the two ends (3) inwards. The pin (2) also comprises a reduced diameter portion which is smaller than the engagement section and the inner diameter of the bearing (54). When the pin is in a relaxed state, the engagement section of the pin engages the inner diameter of the one-way bearing, which permits the device to rotate closed, but prevents rotation in the open direction. When the pin is compressed by squeezing the two ends (3), the pin slides laterally such that the reduced diameter portion is disposed within the one-way bearing, permitting free rotation in either direction.

In one embodiment, the cylinder and one-way bearing assemblies are provided at both ends of the device, which permits greater torque loads on the device in the closed position. It also permits slightly asymmetric application of the device on a wound, where the distal edges of the two opposing members are not exactly parallel. The torsional force acting on the one-way bearing at each end may be different.

Accordingly, a user can with one hand and one motion close the device about a wound, and the device will remain locked in a closed position. The device can be unlocked to release the device to its open position by a simple movement, again permitting one-handed use, if necessary or desired.

The scope of the invention includes alternative mechanical configurations which permit rotation of the two opposing members and a releasable locking or latching of the device into a closed position.

In one embodiment, as shown in FIG. 8, each of the opposing members (4, 6) may have an optional stabilizing pad (22, 24) for balancing the device about a closed wound. Because of the mass of the device, it may have a tendency to sway when in position, closed on a wound. The stabilizing pads (22, 24) prevent or limit that swaying motion. In one embodiment, the stabilizing pads are extended along the length of the distal edge, approximately tangent to the cylinder formed by the closed members and parallel to the surface of the wound. In one embodiment, each of the opposing members (4, 6) defines a number of openings (30), which allow the user to visualize the wound. The openings (30) may also allow access for medical or surgical instruments while the device is in use.

Figure 16:
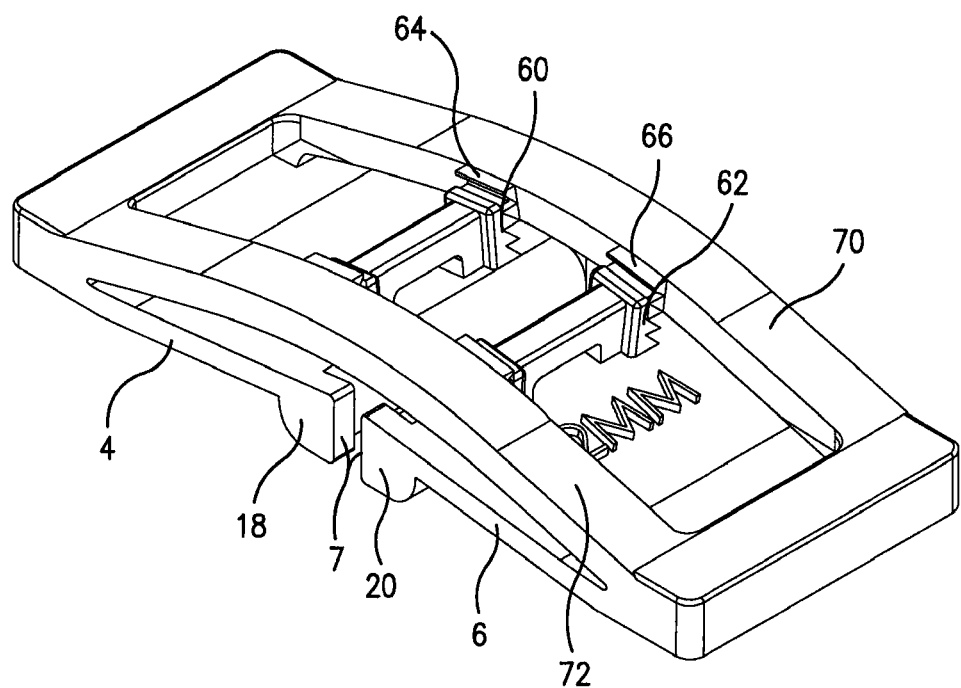
FIG. 16 is an isometric view of one embodiment of a clamp.
Figure 17:
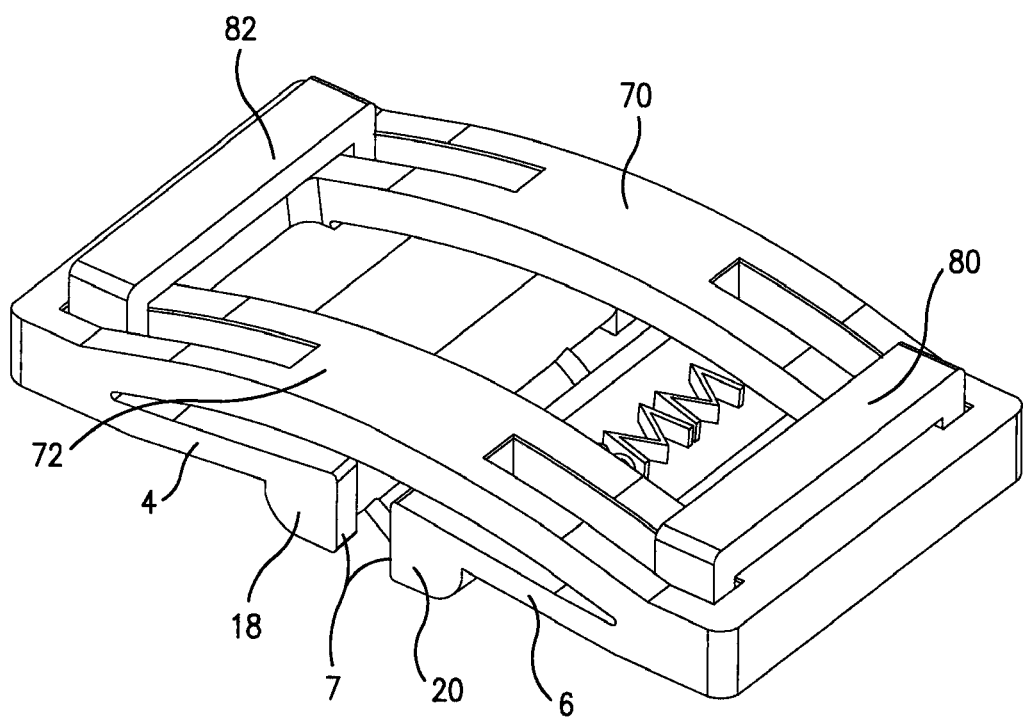
FIG. 17 is an isometric view of one embodiment of a clamp.
Figure 18:
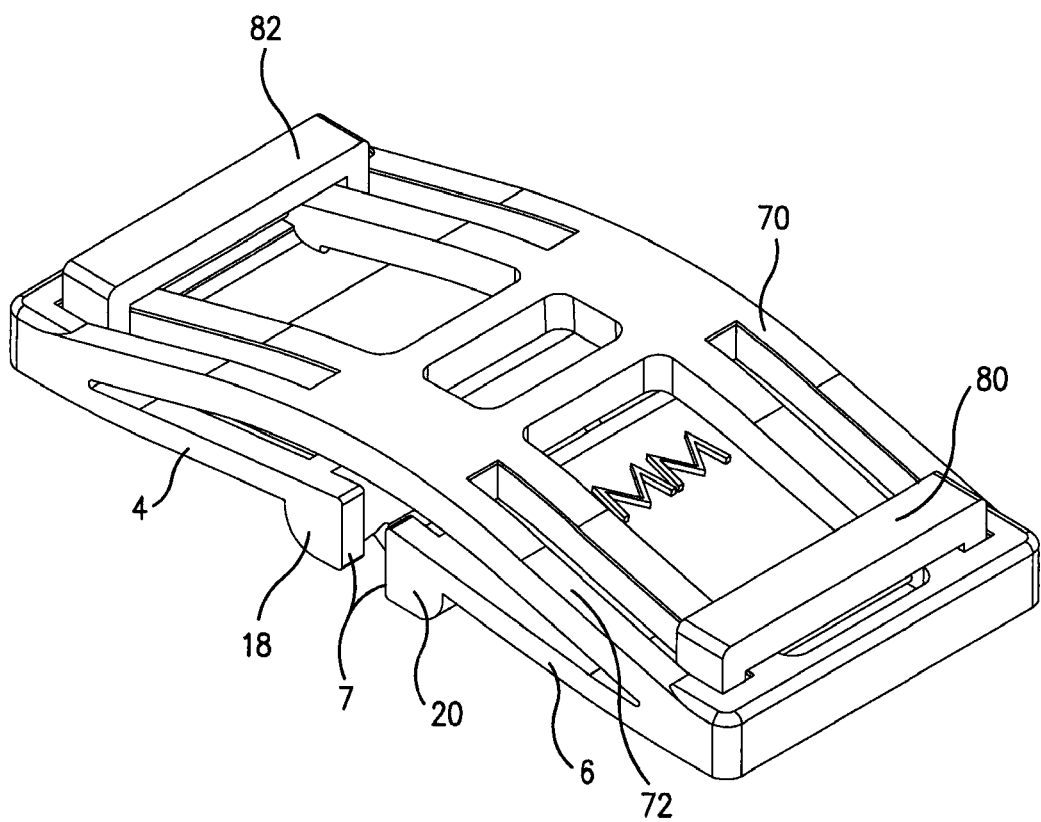
FIG. 18 is an isometric view of one embodiment of a clamp.

In some embodiments, the wound closure device is adapted as a low profile wound closure device which provides for additional flexibility in application, as well as convenience and mobility of the patient upon application. FIGS. 16-18 illustrate embodiments in which the wound closure device is adapted as a clip type device. As shown in FIGS. 16-19 two opposing members (4, 6) are disposed on opposing sides of a central axis, each resiliently moveable between a closed position and open position relative to each other, each of the opposing members having a distal edge. The device further includes skin penetrating means on the distal edge, such as needles, for anchoring the device. A pressure bar (18, 20) is also disposed along each distal edge. A releasable locking means for maintaining the device in the closed position is also included.

Figure 20:
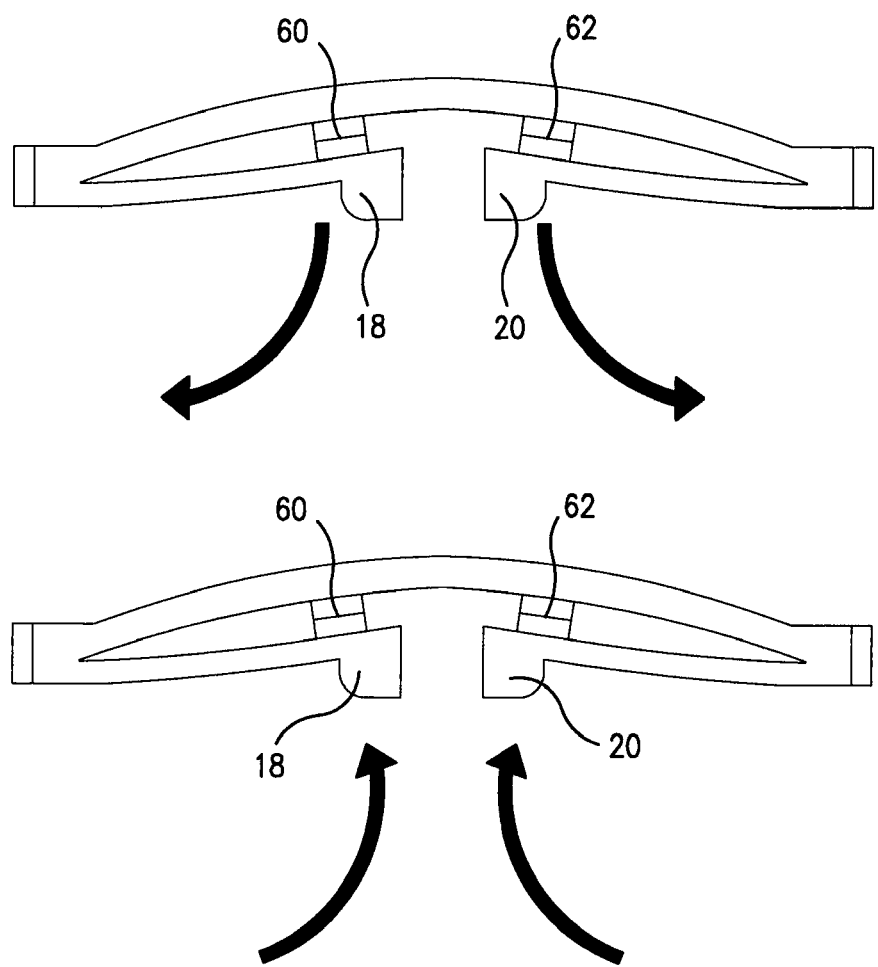
FIG. 20 is a side view of one embodiment of a clamp.

In one embodiment, the wound closure device is a clip type device having ratchets for maintaining the device in the closed position. As shown in FIG. 16, ratchet teeth are disposed on opposing members (4, 6). As shown in FIG. 20, in operation, a pivotal force is applied to the central axis to rotate each pressure bar (18, 20) downward approximately 90° and insert needles into a patient's skin on opposing sides of a wound. The pressure bars are then rotated upward causing the ratchet teeth (60, 62) disposed on each opposing member (4, 6) to engage teeth (64, 66) disposed on connector members (70, 72). Engagement of the teeth locks the pressure bars to the closed position thereby approximating the skin and sealing the wound.

Figure 19:
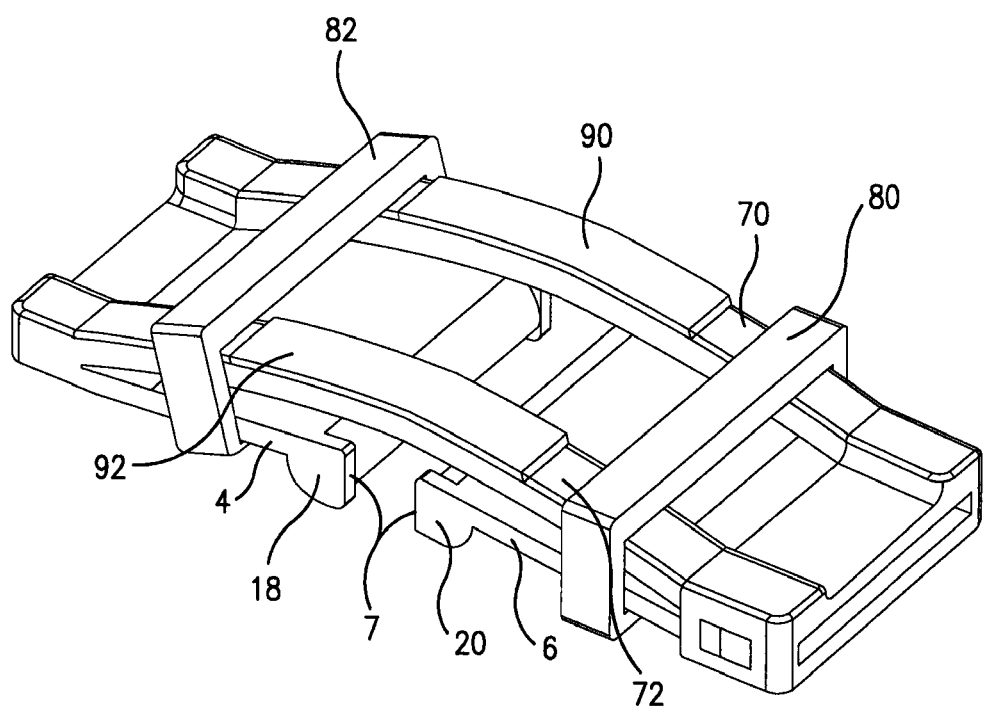
FIG. 19 is an isometric view of one embodiment of a clamp.
Figure 21:
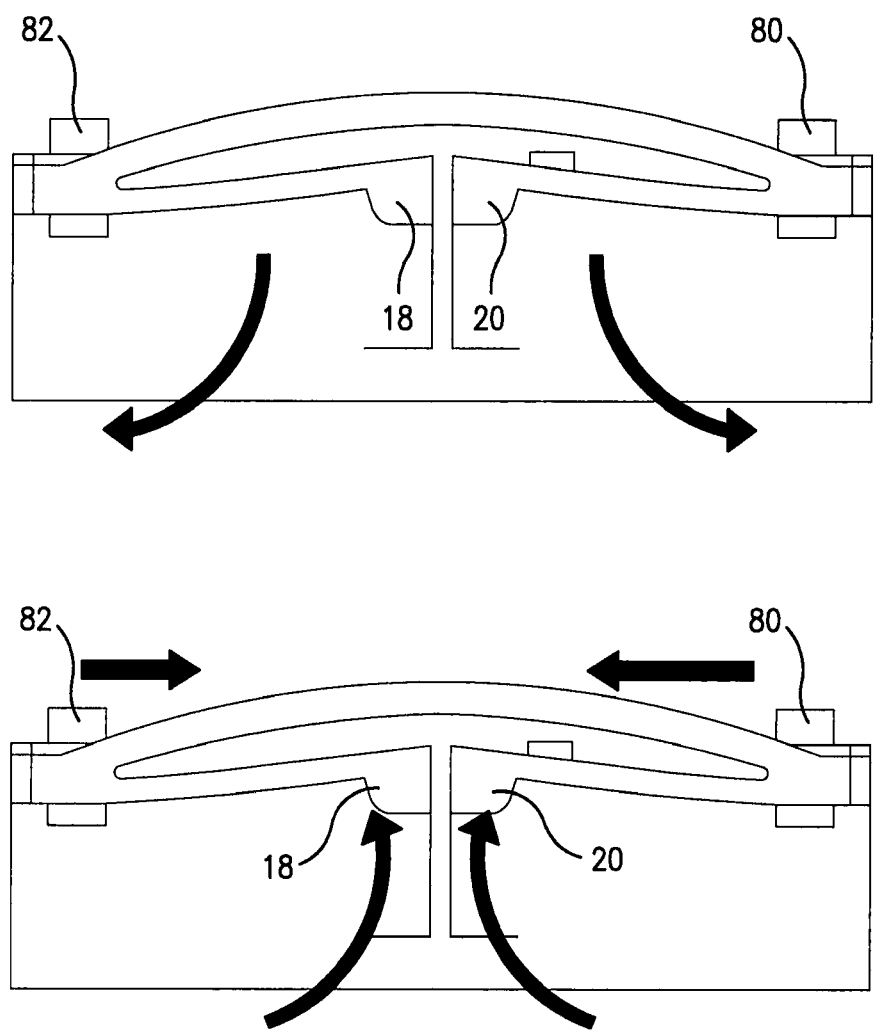
FIG. 21 is a side view of one embodiment of a clamp.

In another embodiment, the wound closure device is a clip type device having closure straps for maintaining the device in the closed position. As shown in FIGS. 17-19, strap members (80, 82) are disposed on opposing sides of the device. As shown in FIG. 21, in operation, a pivotal force is applied to the central axis to rotate each pressure bar (18, 20) downward approximately 90° and insert needles into a patient's skin on opposing sides of a wound. The pressure bars are then rotated upward by relaxing the pivotal pressure. Strap members (80, 82) are then slid along connecting members (70, 72) toward the center axis to lock the pressure bars (18, 20) in the closed position thereby approximating the skin and sealing the wound. The device may further include teeth (90, 92) disposed on connecting members (70, 72) which engage strap members (80, 82) to lock the device in the closed configuration.

Figure 22:
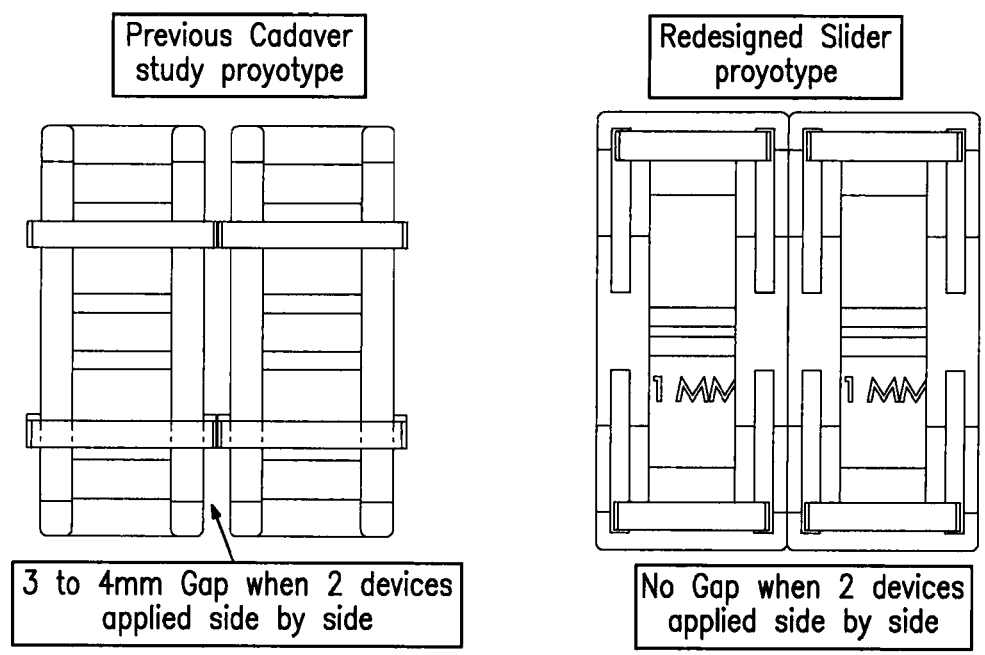
FIG. 22 is a top view of one embodiment of multiple clamps.

In embodiments, multiple would closure devices may be applied to close a wound. For example, 2, 3, 4, 5, 6, 7 or greater wound closure devices may be applied to a wound. In one embodiment, the devices may be aligned side by side along the length of the wound. Depending on the type of wound closure devices used in combination, there may be gaps that are formed between the devices. As shown in FIG. 22, where clip type devices having external closure straps are aligned side by side, a gap exists between each device. As shown in FIG. 22, where clip type devices having internal closure straps are aligned side by side, there is no gap between each device.

In embodiments, the wound closure device may be configured with an accessory component adapted to directly or indirectly secure or anchor the device to another medical instrument. The wound closure device is anchored to the skin via pressure bars and skin penetrating means. The accessory component allows for rapid attachment of the accessory to the wound closure device, and takes advantage of the anchorage of the wound closure device into the skin to secure or anchor another medical instrument, such as a tube.

Attachment of accessory instruments to the wound closure device allows a variety of additional indications for use of the device. For example, an accessory port may be used as a means of inserting a device into a wound for delivery of therapeutics such as hemostatic agents, infection control agents, agents to reduce clot lysis and the like. Additionally, an accessory port may be used as a means inserting a device into a wound to remove material, such as a vacuum tube/dressing to create negative pressure through a suction device, or a needle decompression device to remove air from a chest wound.

As such, in one aspect, the present disclosure provides a method for insertion and anchorage of a needle decompression needle for use with a chest wound to perform needle decompression; e.g., to avoid conversion of an open pneumothorax into a tension pneumothorax.

In one aspect, the present disclosure provides a method for insertion and anchorage of a catheter or needle for insertion of therapeutic agents into a hematoma; e.g., one created following use of the wound closure device of the invention in the fluid-tight sealing of an open wound. Such a technique could be necessary with a vacuum drainage tube to remove fluid accumulation, or similarly to remove air from a cavity by inserting a needle, just as an example. This configuration of the device is well-suited to immediate application at the point of injury. By using the wound closure device to create a hematoma for open wound control, it becomes possible to direct other materials and agents to the hematoma, such as clotting agents to accelerate clotting, antibiotics to reduce infection, and agents to reduce clot lysis.

In one aspect, the present disclosure provides a method to maintain vacuum pressure on a wound cavity by means of anchoring an inserted suction tube and suction device to the wound closure device.

In one aspect, the present disclosure provides a method for anchoring the needle/tube for insertion or removal of material to/from the wound cavity by attachment of the device to the dermis surrounding the wound by operating the pressure bars of the wound closure device to secure it to the dermis and keep the device from slipping when the patient moves or is moved.

In one aspect, the present disclosure provides a method for connecting an accessory component to the wound closure device by means of threaded holes (such as but not limited to luer lock threading), quick-connect ends, pressure fittings, adaptors, and the like.

Figure 23:
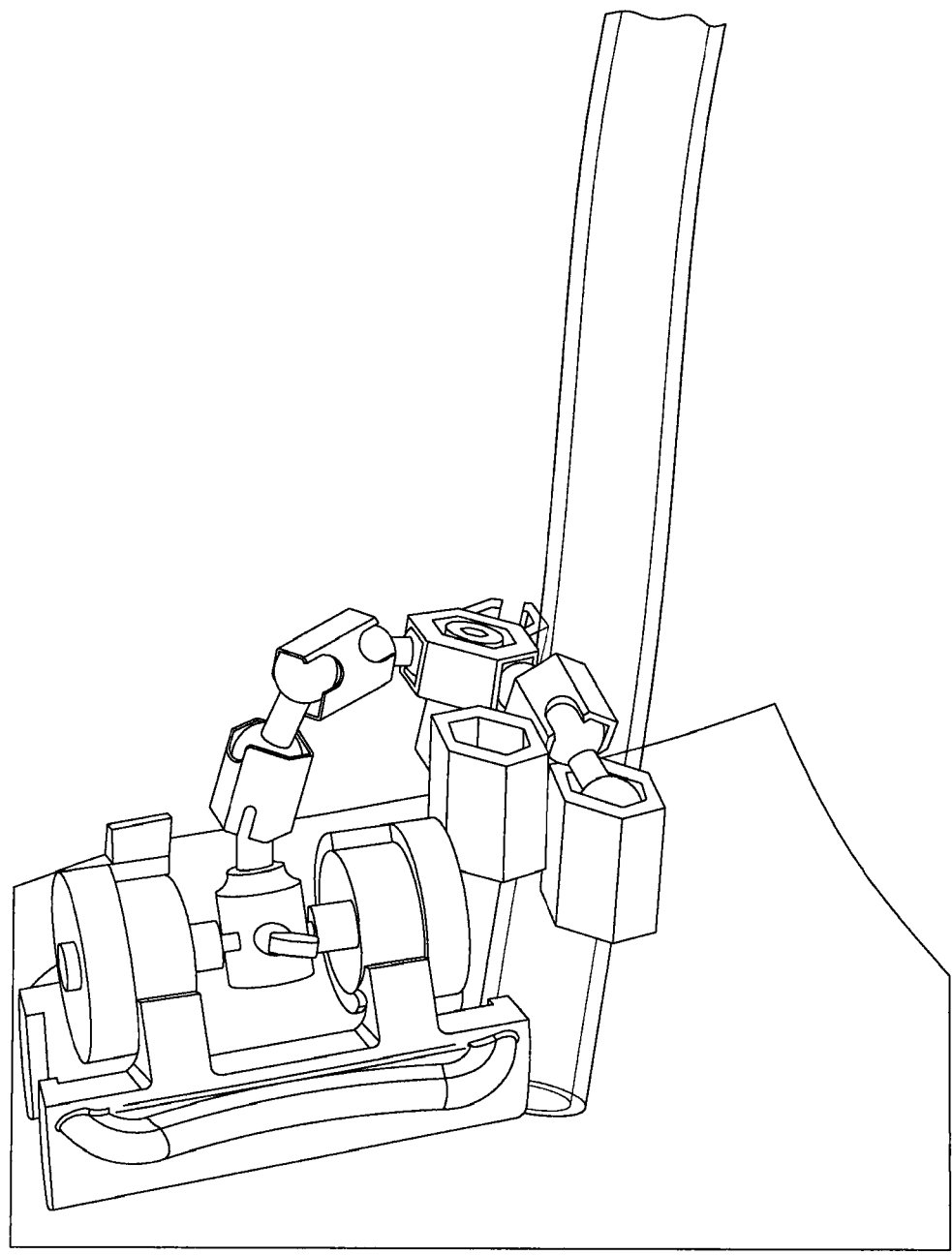
FIG. 23 is a perspective view of one embodiment of a clamp and accessory component.
Figure 24:
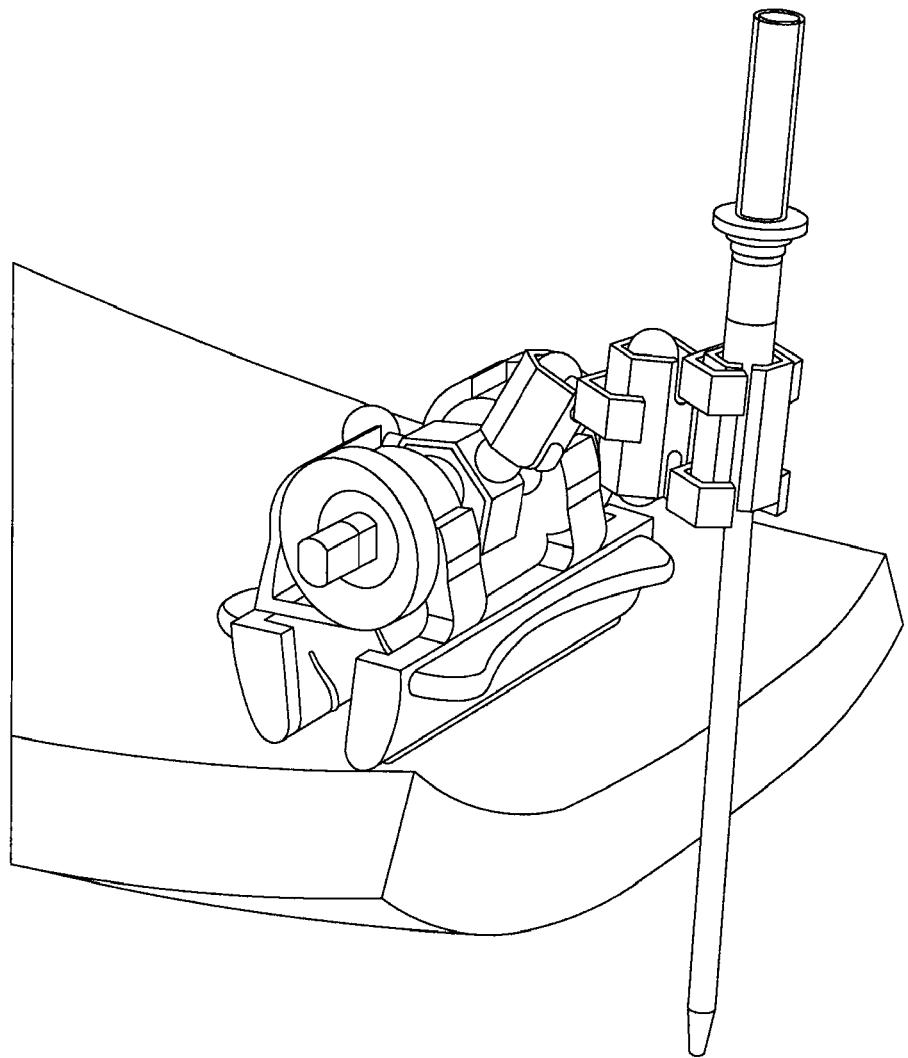
FIG. 24 is a perspective view of one embodiment of a clamp and accessory component.

For example, FIG. 23 shows an accessory component attached to a wound closure device and securing a tube which enters the patient near placement of the closure device. The accessory component (95) includes an articulating arm (100) secured along the longitudinal axis of the closure device which can be pivoted to any side of the closure device allowing the accessory component to operate in multiple geometries. In a further example, FIG. 24 shows an accessory component (95) securing a catheter to a wound closure device.

Figure 25:
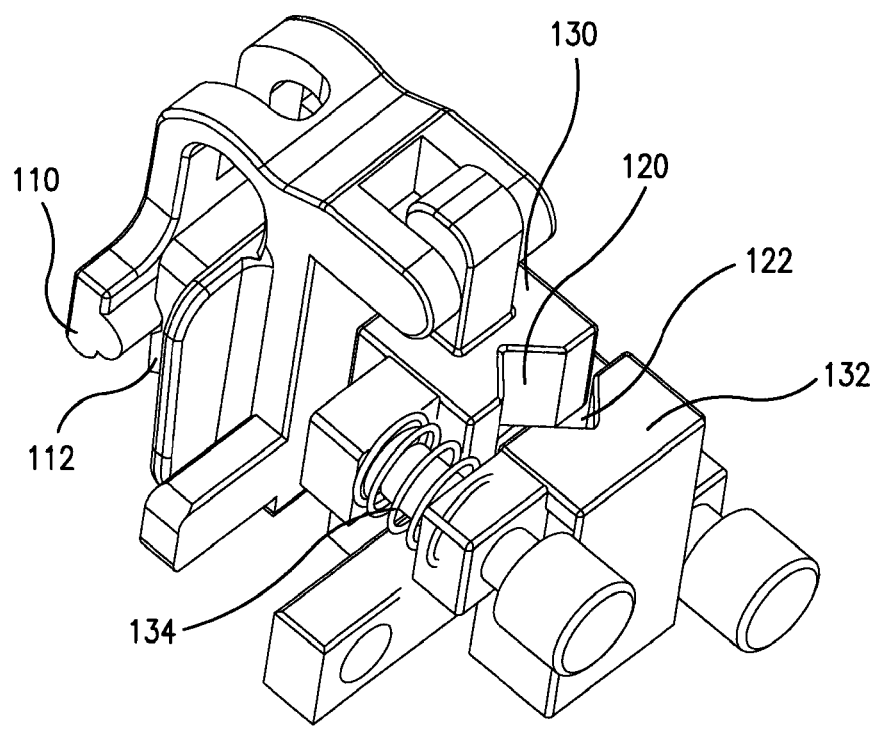
FIG. 25 is a perspective view of one embodiment of an accessory component.

In a further embodiment, the wound closure device includes an accessory component as shown in FIG. 25. The accessory component includes attachment surfaces (110, 112) that are mounted to a wound closure device. A tube may be entered through grooves (120, 122) disposed in plates (130, 132) which are pressed together via springs (134), thereby holding the tube in place and anchoring the wound closure device to the inserted tube.

Figure 26:
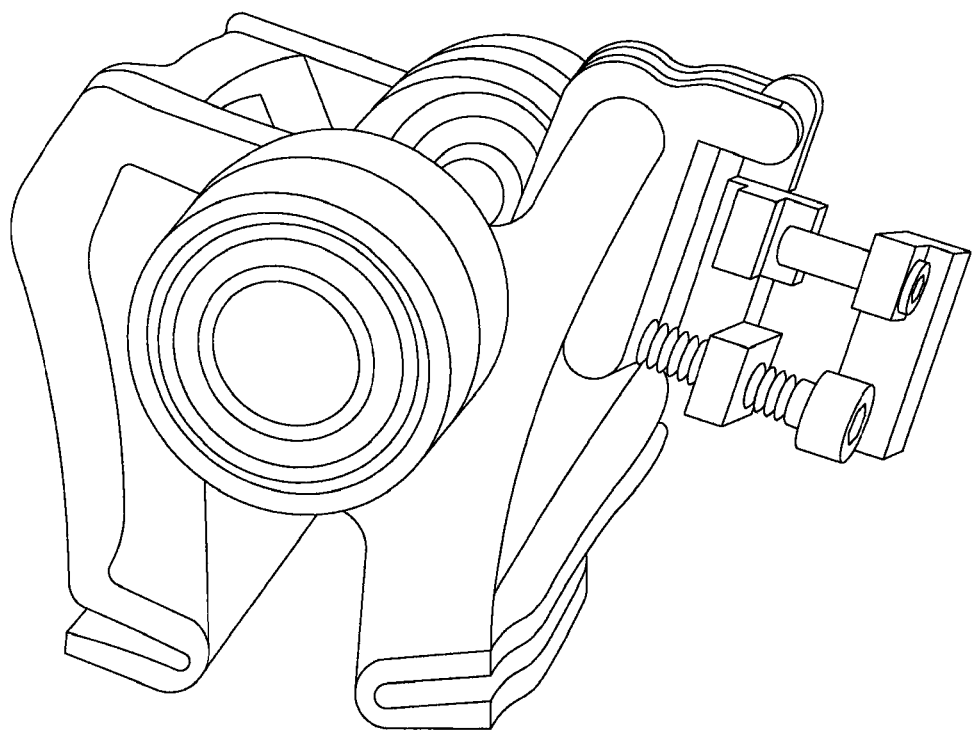
FIG. 26 is a perspective view of one embodiment of a clamp and accessory component.
Figure 27:
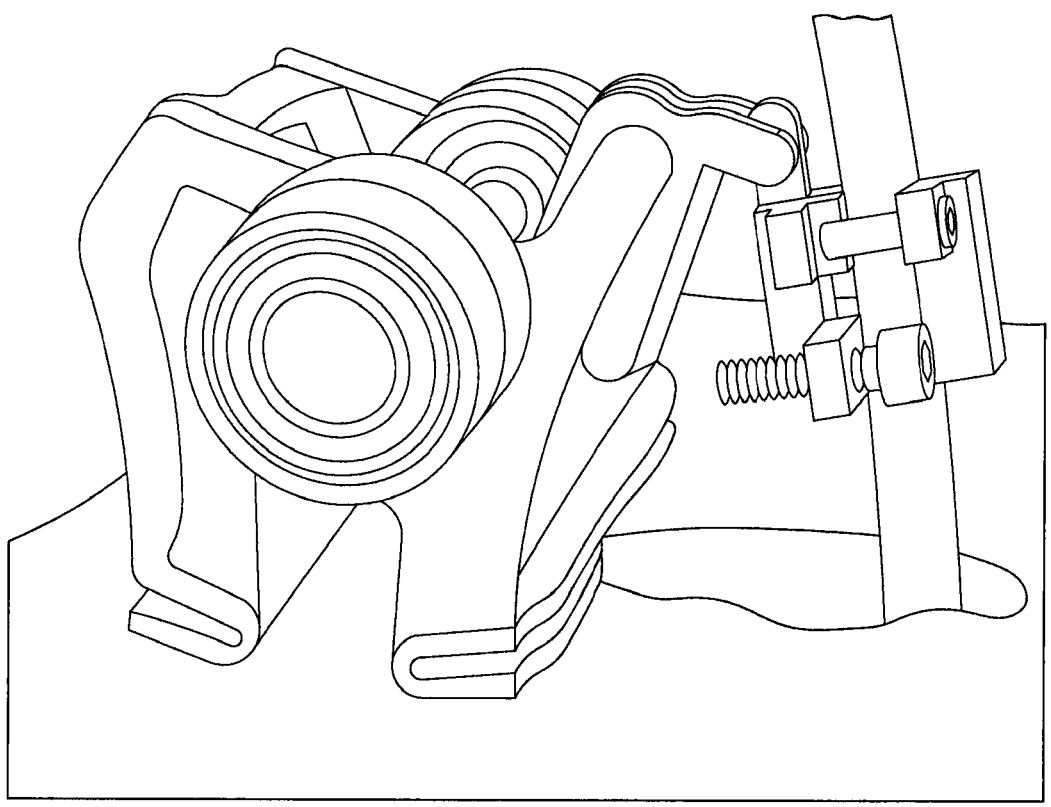
FIG. 27 is a perspective view of one embodiment of a clamp and accessory component.

In one embodiment, the wound closure device includes an accessory component as shown in FIGS. 26 and 27. The accessory component is shown mounted to a wound closure device. In this configuration, a tube is secured to the wound closure device adjacent the wound closure device.

Figure 28:
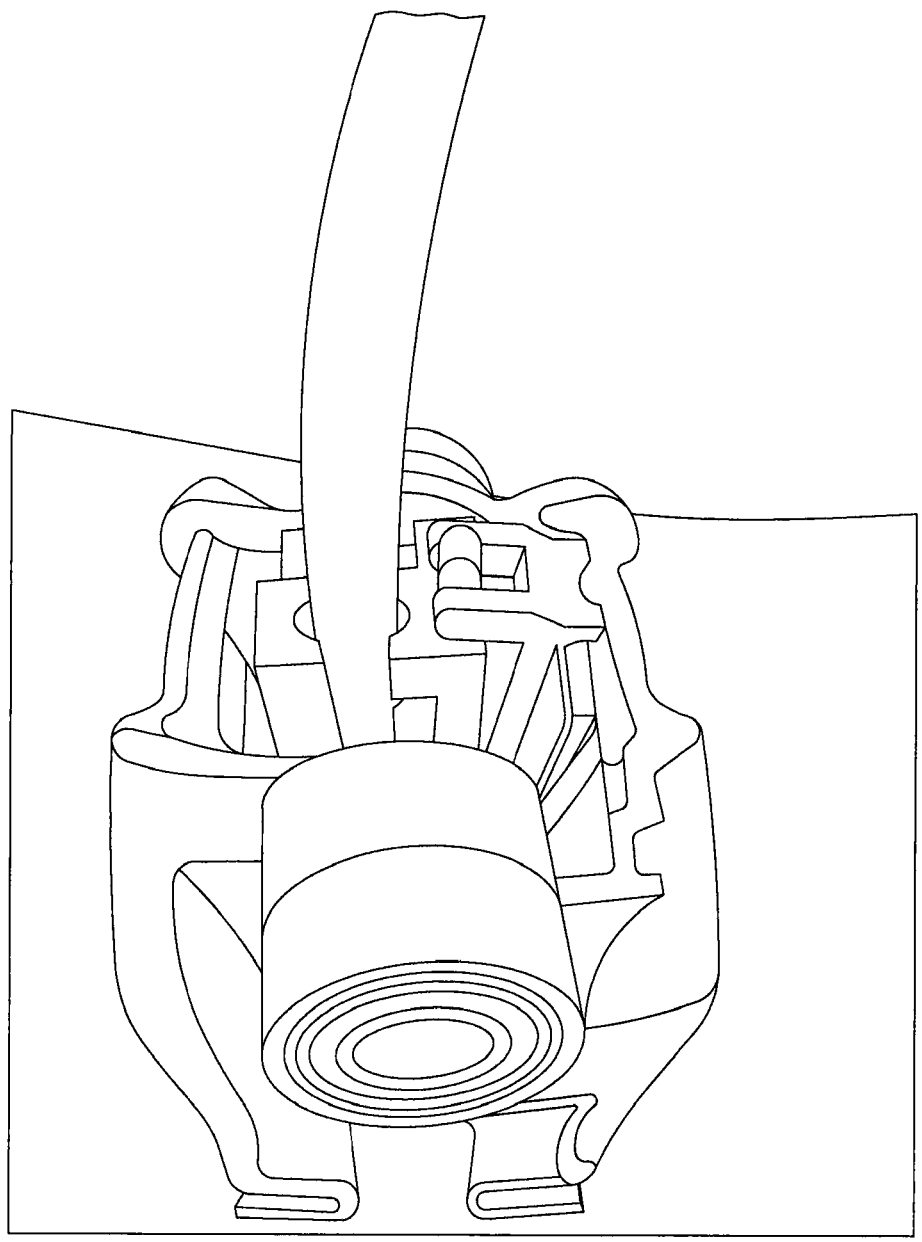
FIG. 28 is a perspective view of one embodiment of a clamp and accessory component.

In one embodiment, the wound closure device includes an accessory component as shown in FIG. 28. The accessory component is shown mounted to a wound closure device. In this configuration, a tube is secured to the wound closure device such that the tube traverses through a central region of the device, running through opposing members (18, 20).

Figure 29:
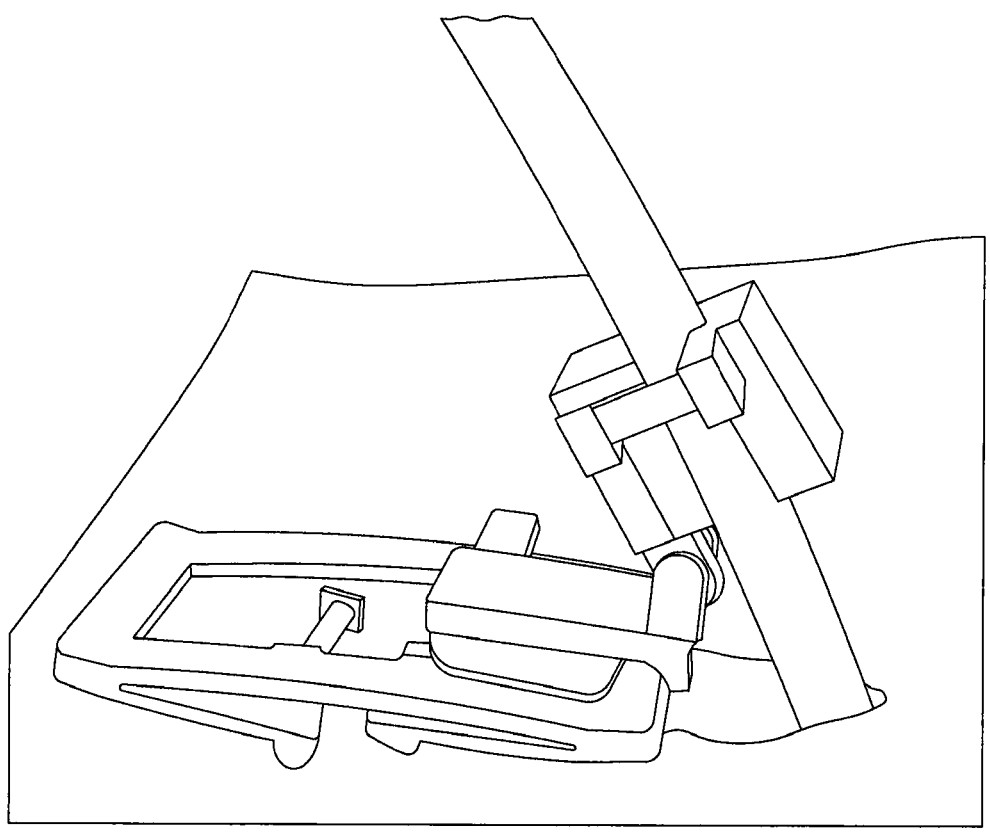
FIG. 29 is a perspective view of one embodiment of a clamp and accessory component.

In one embodiment, the wound closure device includes an accessory component as shown in FIG. 29. The accessory component is shown mounted to a clip type wound closure device. In this configuration, a tube is secured to the wound closure device adjacent the wound closure device.

Figure 30:
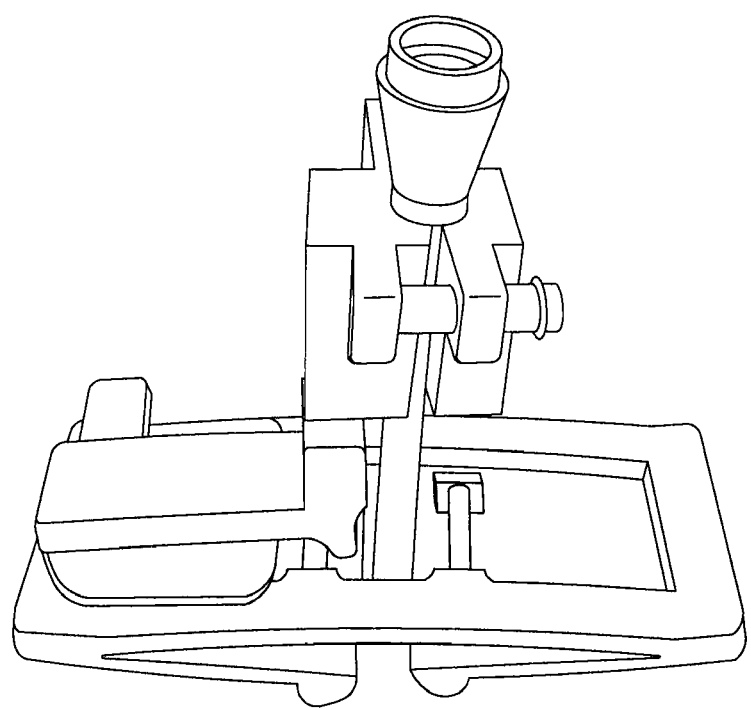
FIG. 30 is a perspective view of one embodiment of a clamp and accessory component.

In one embodiment, the wound closure device includes an accessory component as shown in FIG. 30. The accessory component is shown mounted to a clip type wound closure device. In this configuration, a medical instrument is secured to the wound closure device such that the instrument traverses through a central region of the device.

Figure 31:
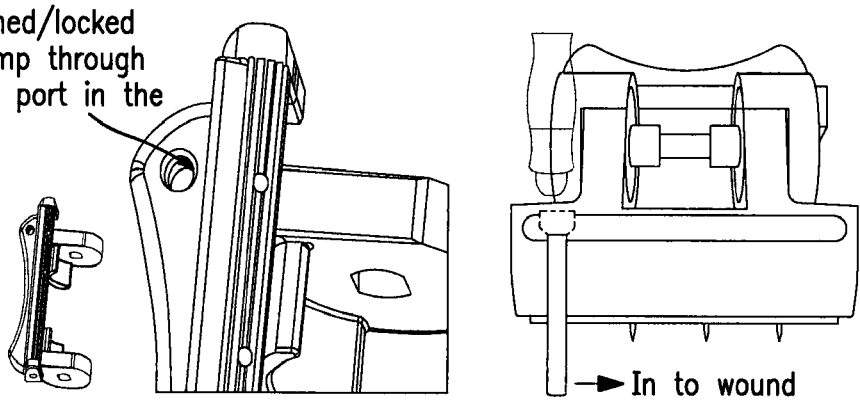
FIG. 31 is a series of illustrations of one embodiment of a clamp and accessory component.

As discussed herein, allowing for attachment of accessories to the wound closure device of the inventions makes the device capable of use in contexts other than just wound closure. In one embodiment, the wound closure device includes an accessory component configured as a port directly disposed in the wound closure device as shown in FIG. 31. The wound closure device of FIG. 31, includes a threaded port (120) disposed in an opposing member of the device, therefore allowing for use of the device to provide a port system.

In various embodiments, the wound closure device includes an accessory component configured as a port which can be used as an injection port, thereby allowing for methods of wound access to attach insertion devices to inject hemostatic agent into a wound site while at the same time approximating wounded skin with pressure to actively clot blood and staunch blood flow at active bleeding wound sites to reduce the risk of exsanguination. Such a device could also be used to insert other materials into the wound, such as therapeutic agents, and the like.

In one embodiment, the port is used as an vacuum access port, which allows for methods of wound access to provide vacuum-assisted care to collapse an interior wound cavity with light vacuum while at the same time approximating wounded skin with pressure to actively reduce the size of the cavity and promote healing. A vacuum access port created according to the invention may also be used to remove chest fluid accumulation, or similarly to remove air from the pleural cavity of the sealed chest by inserting a vacuum tube and pump.

In various embodiments the port functions as a quick connect adaptor, a luer lock, or other port, as a means to fix a wound access device to the skin. Means for permitting the insertion of solid valves, needles, trocars or other devices into a wound prior to closure or after closure of the device is envisioned.

In more particular embodiments, the wound closure device further includes one or more accessory components such as: one or more ports having a threading with a known pitch; means for attaching the one or more port to a needle or tube for use by an accessory, an adapter, a thread on the needle, a pressure fitting, or other attachment mechanism; means for permitting the needle or tube to be fixed from migrating into or out of the wound by attachment to the closure device; means for attaching one or more ports to a syringe or pump for use by an adapter, a thread on the syringe or pump, a pressure fitting, or other attachment mechanism; means for permitting the syringe or pump to be fixed from migrating by attachment to the gripping bar; means for viewing the accessory placement for accurate placement by at least one visual port.

In various particular embodiments, the wound closure device includes pressure bars having various geometries that increase friction with skin. For example, a pressure bar may have a non-uniform surface, such as serrations, protrusions or teeth to improve the grasp on the skin for an air-tight seal which is required for suction and vacuum applications.

In one embodiment, wound closure device is secured to and anchors a drainage tube. As such, in certain aspects the closure device is suitable for treating tension pneumothorax and for treating hemothorax.

Figure 32:
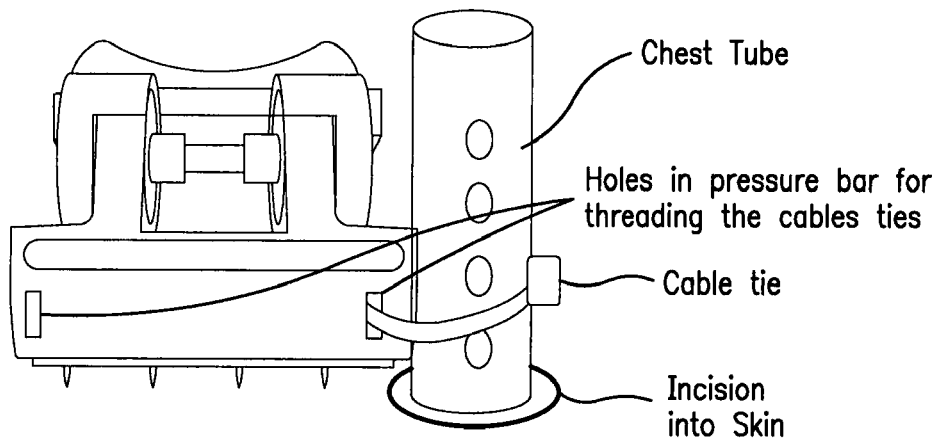
FIG. 32 is a side view of one embodiment of a clamp and accessory component.

In one embodiment, the wound closure device includes a means for securing a medical component to the closure device via straps or cable ties. As shown in FIG. 32, the wound closure device may is configured with slots (140, 142) in the pressure bar (18) allowing a self-locking cable tie to attach to the closure device. In the embodiment shown, the cable tie is looped and tightened around a drainage tube, the cable tie fastens the drainage tube to the clamp. Due to the self-locking mechanism of the tie, the drainage tube cannot be pulled free from the clamp. Once the device is attached to the skin, and the tube is attached to the device, the tube is fixed to the body and cannot migrate. One skilled in the art would understand that a variety of medical components may be secured to the device in this manner in addition to drainage tubes.

In one embodiment, the wound closure device is provided as a kit comprising a wound closure device in a sterile package, which may be opened with one hand. Therefore, it may be seen that a user may take the sterile package, open it and remove the device which is stored in its closed position, open it with one hand, place it on a wound, and close it, all with one hand and in very little time.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Wound Closure Device with Port

The wound closure device was constructed having a threaded port integrated into an opposable member of the device. The prototype device was used on a sucking chest wound. A catheter was inserted into the port prior to wound closure by the device. The catheter was inserted into the wound, followed by closing the skin to create an air tight seal with the exception of the catheter itself. With the wound closure device in the closed position, it approximated a threaded port for needle decompression of a potential pneumothorax. The catheter was determined to be secure when subjected to pulling force. The device was determined to be functional as the only air escaping from the closed sucking chest wound (air tight seal) was through the catheter of the device. The catheter remained where it was, did not go further in or further out.

Example 2

Wound Closure Device with Cable Ties

The wound closure device with cable ties embedded into the pressure bars of the device was constructed as shown in FIG. 32. Holes were disposed into the pressure bars through which cable ties were threaded to attach the cable tie/chest tube to the skin of the patient. A chest tube with a Heimlich valve was inserted into a sucking chest wound that caused a pneumothorax. Embedding the wound closure device into the skin, the cable tie was looped around the chest tube and tightened. The chest tube was determined to be anchored into the wound and could not be forced deeper into the wound, nor pulled out.

Although the invention has been described with reference to the above example, it will be understood that modifications and variations are encompassed within the spirit and scope of the invention. Accordingly, the invention is limited only by the following claims.

What is claimed is:

1. A wound closure device comprising:
   (a) a first opposing member and a second opposing member engaged about a longitudinal axis, each pivotally moveable around the longitudinal axis between a closed position and an open position relative to each other, each of the opposing members having a proximal edge adjacent the longitudinal axis and a distal edge;
   (b) a skin penetrating means for anchoring the device;
   (c) a pressure bar along each of the distal edges;

(d) a releasable locking means for biasing or maintaining the device in the closed position, wherein the releasable locking means comprising a one-way cylindrical bearing disposed between the two opposing members, and a longitudinal pin disposed within the bearing, wherein the one-way bearing rotates with one opposing member of the first and second opposing members, and the pin rotates with the other opposing member of the first and second opposing members, and wherein the pin comprises an engagement section which engages the bearing to rotate freely in one direction but not the other direction, and a reduced diameter section where the pin freely rotates in either direction, and the pin is moveable longitudinally to slide the reduced diameter section into and out of the bearing; and (e) an accessory component.

2. The device of claim 1, wherein each of the opposing members comprises an end closure member substantially perpendicular to the distal edge and aligned with an opposing end closure member.

3. The device of claim 1, wherein the skin penetrating means comprises a plurality of needles disposed along each of the pressure bars.

4. The device of claim 3, wherein the needles are of sufficient length to be configured in penetrating the skin and piercing underlying tissue.

5. The device of claim 3, wherein the needles are straight or are curved with a radius of curvature substantially similar to a radius of curvature of the opposing members.

6. The device of claim 1, wherein the two opposing members frictionally engage each other to remain in the closed position.

7. The device of claim 6, wherein the frictional engagement is enhanced by a plurality of longitudinal ridges on one or both of the opposing members.

8. The device of claim 1, wherein the device comprises an additional releasable locking means at an end of the device.

9. The wound closure device of claim 1, further comprising a medical instrument coupled to the accessory component.

10. The wound closure device of claim 9, wherein the medical instrument is selected from a needle, tube, catheter, and cannula.

11. The wound closure device of claim 1, further comprising an integrated port.

12. The wound closure device of claim 1, wherein the accessory component comprises means for securing a medical device to the wound closure device.

13. The wound closure device of claim 12, wherein the accessory component comprises an articulated arm.

14. A method for performing a medical procedure on a subject, comprising:
(a) deploying the wound closure device of claim 1 to a wound of the subject; and
(b) locking the wound closure device in the closed position, thereby performing the medical procedure on the subject.

15. The method of claim 14, further comprising coupling a medical instrument to the wound closure device.

* * * * *